(12) United States Patent
Wilson (10) Patent No.: US 7,806,865 B1
(45) Date of Patent: Oct. 5, 2010

(54) PRESSURIZED IRRIGATION SQUEEZE BAND

(75) Inventor: Daniel J. Wilson, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 12/469,354

(22) Filed: May 20, 2009

(51) Int. Cl.
*A61M 37/00* (2006.01)

(52) U.S. Cl. .................................. 604/131; 604/132

(58) Field of Classification Search ......... 600/400–402; 604/65–67, 118–121, 131–133, 289, 294, 604/297, 298
See application file for complete search history.

(56) References Cited

U.S. PATENT DOCUMENTS

| | | | |
|---|---|---|---|
| 3,589,363 A | 6/1971 | Banko et al. | |
| 4,029,094 A | 6/1977 | Winicki | |
| 4,184,510 A | 1/1980 | Brumbach et al. | |
| 4,223,676 A | 9/1980 | Wuchinich et al. | |
| 4,246,902 A | 1/1981 | Martinez | |
| 4,493,694 A | 1/1985 | Wuchinich | |
| 4,515,583 A | 5/1985 | Sorich | |
| 4,589,415 A | 5/1986 | Haaga | |
| 4,609,368 A | 9/1986 | Dotson, Jr. | |
| 4,813,927 A | 3/1989 | Morris et al. | |
| 4,869,715 A | 9/1989 | Sherburne | |
| 4,900,301 A | 2/1990 | Morris et al. | |
| 4,909,786 A | 3/1990 | Gijeslhart et al. | |
| 4,922,902 A | 5/1990 | Wuchinich et al. | |
| 4,989,583 A | 2/1991 | Hood | |
| 5,032,111 A | 7/1991 | Morris et al. | |
| 5,047,009 A | 9/1991 | Morris et al. | |
| 5,154,694 A | 10/1992 | Kelman | |
| 5,160,317 A | 11/1992 | Costin | |
| 5,178,606 A | 1/1993 | Ognier et al. | |
| 5,207,645 A * | 5/1993 | Ross et al. | 604/141 |
| 5,279,547 A | 1/1994 | Costin | |
| 5,308,335 A * | 5/1994 | Ross et al. | 604/141 |
| 5,330,431 A * | 7/1994 | Herskowitz | 604/153 |
| 5,342,313 A * | 8/1994 | Campbell et al. | 604/153 |
| 5,359,996 A | 11/1994 | Hood | |
| 5,399,166 A * | 3/1995 | Laing | 604/146 |
| 5,403,276 A | 4/1995 | Schechter | |
| 5,520,633 A | 5/1996 | Costin | |
| 5,586,973 A | 12/1996 | Lemaire et al. | |
| 5,591,127 A | 1/1997 | Barwick, Jr. et al. | |
| 5,643,304 A | 7/1997 | Schechter et al. | |
| 5,685,840 A | 11/1997 | Schechter et al. | |
| 5,700,240 A | 12/1997 | Barwick, Jr. et al. | |
| 5,733,256 A | 3/1998 | Costin | |
| 5,766,146 A | 6/1998 | Barwick, Jr. | |
| 5,776,105 A * | 7/1998 | Corn | 604/174 |

(Continued)

FOREIGN PATENT DOCUMENTS

WO       WO 9520373       11/1995

*Primary Examiner*—Nicholas D Lucchesi
*Assistant Examiner*—Gerald Landry, II
(74) *Attorney, Agent, or Firm*—Kenneth D. Bassinger (57) ABSTRACT

A pressurized infusion device has a flexible band with first and second ends, a curved base, and a bag containing fluid. The bag is located between the flexible band and the curved base. The second end of the flexible band is coupled to a shaft. A motor is also coupled to the shaft. The motor is actuated to turn the shaft and produce tension in the band thereby changing the fluid pressure in the bag.

8 Claims, 5 Drawing Sheets

U.S. PATENT DOCUMENTS

| | | |
|---|---|---|
| 5,836,909 A | 11/1998 | Cosmescu |
| 6,083,193 A | 7/2000 | Kadziauskas |
| 6,096,007 A * | 8/2000 | Haan et al. .................. 604/147 |
| 6,155,975 A | 12/2000 | Urich et al. |
| 6,179,808 B1 | 1/2001 | Boukhny et al. |
| 6,454,132 B2 * | 9/2002 | Campion ..................... 222/96 |
| 6,491,661 B1 | 12/2002 | Boukhny et al. |
| 6,699,212 B1 | 3/2004 | Kadziauskas et al. |
| 6,908,452 B2 * | 6/2005 | Diaz et al. .................. 604/131 |
| 2002/0077587 A1 * | 6/2002 | Boukhny et al. .............. 604/67 |

\* cited by examiner

PRESSURIZED IRRIGATION SQUEEZE BAND

BACKGROUND OF THE INVENTION

The present invention relates to phacoemulsification surgery and more particularly to a device that better regulates infusion pressure.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Throughout the procedure, irrigating fluid is pumped into the eye, passing between the irrigation sleeve and the cutting needle and exiting into the eye at the tip of the irrigation sleeve and/or from one or more ports, or openings, cut into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

A common phenomena during a phacoemulsification procedure arises from the varying flow rates that occur throughout the surgical procedure. Varying flow rates result in varying pressure losses in the irrigation fluid path from the irrigation fluid supply to the eye, thus causing changes in pressure in the anterior chamber (also referred to as Intra-Ocular Pressure or IOP.) Higher flow rates result in greater pressure losses and lower IOP. As IOP lowers, the operating space within the eye diminishes.

Another common complication during the phacoemulsification process arises from a blockage, or occlusion, of the aspirating needle. As the irrigation fluid and emulsified tissue is aspirated away from the interior of the eye through the hollow cutting needle, pieces of tissue that are larger than the diameter of the needle's bore may become clogged in the needle's tip. While the tip is clogged, vacuum pressure builds up within the tip. The resulting drop in pressure in the anterior chamber in the eye when the clog is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

Various techniques have been attempted to reduce this surge, such as by venting the aspiration line or otherwise limiting the buildup of negative pressure in the aspiration system. However, there remains a need for improved phacoemulsification devices, including irrigation systems that reduce post-occlusion surge as well as maintain a stable IOP throughout varying flow conditions.

SUMMARY OF THE INVENTION

In one embodiment consistent with the principles of the present invention, the present invention is a pressurized infusion device comprising a flexible band having first and second ends, a curved base, and a bag containing fluid. The bag is located between the flexible band and curved base. The second end of the flexible band is coupled to a shaft. A motor is also coupled to the shaft. The motor is actuated to turn the shaft and produce tension in the band thereby changing the fluid pressure in the bag.

In another embodiment consistent with the principles of the present invention, the present invention is a pressurized infusion system for an ophthalmic surgical machine. The pressurized infusion system comprises a flexible band having first and second ends; a curved base; a bag containing irrigating fluid, the bag located between the flexible band and curved base; an irrigation line coupled to the bag; a pressure sensor for reading pressure in the irrigation line; a motor coupled to a shaft, the second end of the band coupled to the shaft; and a controller, the controller receiving an input from the irrigation pressure sensor to control the motor. When the motor is actuated to turn the shaft, tension is produced in the band to change pressure in the bag.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
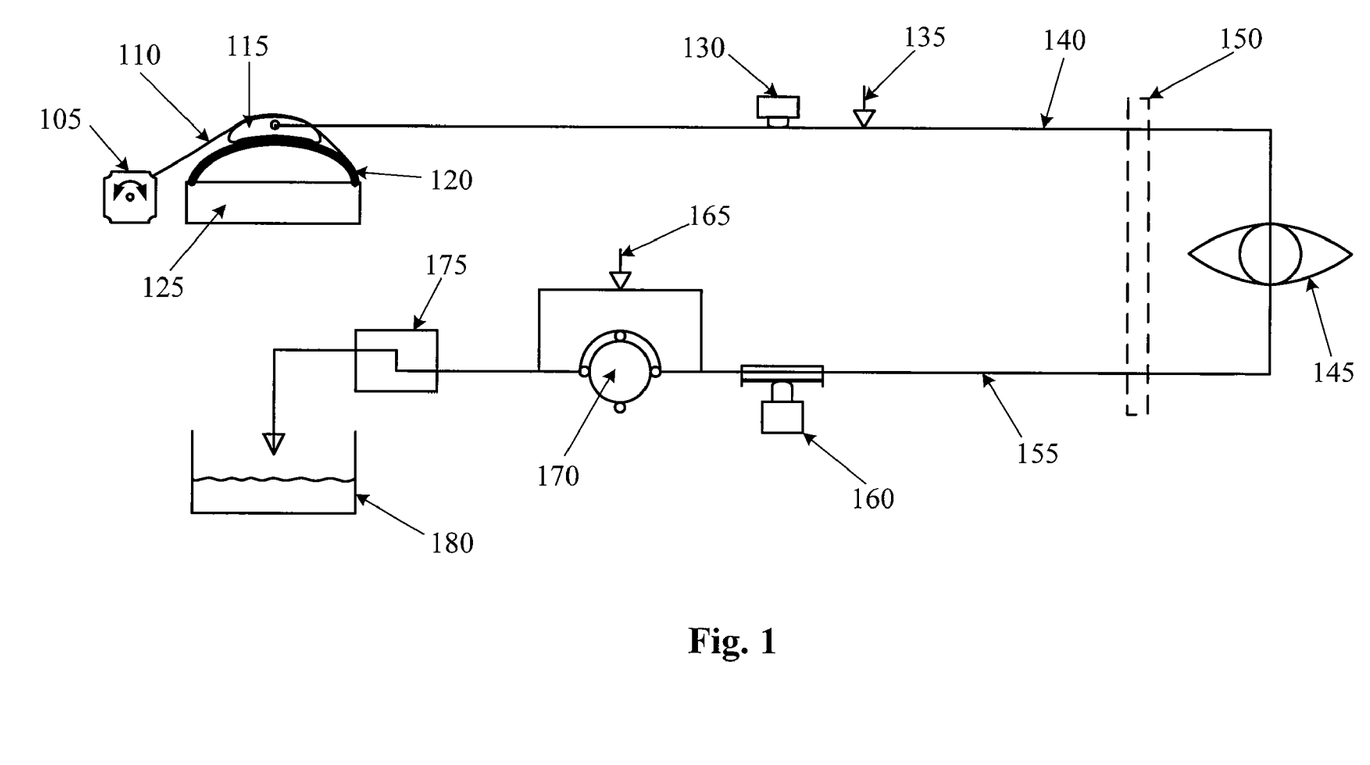
FIG. 1 is a diagram of the components in the fluid path of a phacoemulsification system including a pressurized irrigation squeeze band according to the principles of the present invention.

FIG. 1 is a diagram of the components in the fluid path of a phacoemulsification system including a pressurized irrigation squeeze band according to the principles of the present invention. FIG. 1 depicts the fluid path through the eye 145 during cataract surgery. The components include a motor 105, a band 110, a bag 115, a curved base 120, a frame 125, an irrigation pressure sensor 130, an irrigation valve 135, an irrigation line 140, a hand piece 150, an aspiration line 155, an aspiration pressure sensor 160, a vent valve 165, a pump 170, a reservoir 175 and a drain bag 180. The irrigation line 140 provides irrigation fluid to the eye 145 during cataract surgery. The aspiration line 155 removes fluid and emulsified lens particles from the eye during cataract surgery.

In one embodiment of the present invention, a bag 115 contains irrigation fluid for use during cataract surgery. The bag 115 is located between band 110 and curved base 120. Curved base 120 is mounted to frame 125. A motor 105 has a shaft (not shown) that is attached to one end of band 110. The other end of band 110 is fixed to the curved base 120 or the frame 125. In this manner, the bag 115 can be squeezed between band 110 and curved base 120. When motor 105 is actuated so that the shaft (not shown) to which motor 105 is coupled turns, the band 110 is wound around the shaft (not shown) thereby squeezing bag 110 against curved base 120. This acts to squeeze irrigation fluid out of bag 110. This is shown more clearly in subsequent drawings.

When irrigation fluid is squeezed out of bag 110, it travels through irrigation line 140 and into the eye 145. An irrigation pressure sensor 130 measures the pressure of the irrigation fluid in irrigation line 140. An optional irrigation valve 135 is also provided for on/off control of irrigation. Irrigation pressure sensor 130 is implemented by any of a number of commercially available fluid pressure sensors. Irrigation pressure sensor 130 provides pressure information to a controller (not shown) that operates motor 105. The operation of motor 105 (and attached band 110) controls the pressure of the irrigation fluid exiting bag 115.

Motor 105 can be a DC motor, stepper motor, or other type of motor which can be precisely controlled. In other embodiments of the present invention, motor 105 can be any type of mechanism that is capable of exerting a force on band 110.

A hand piece 150 is placed in the eye 145 during a phacoemulsification procedure. The hand piece 150 has a hollow needle (not shown) that is ultrasonically vibrated in the eye to break up the diseased lens. A sleeve located around the needle provides irrigation fluid from irrigation line 140. The irrigation fluid passes through the space between the outside of the needle and the inside of the sleeve. Fluid and lens particles are aspirated through the hollow needle. In this manner, the interior passage of the hollow needle is fluidly coupled to aspiration line 155. Pump 170 draws the aspirated fluid from the eye 145. An aspiration pressure sensor 160 measures the pressure in the aspiration line. An optional vent valve can be used to vent the vacuum created by pump 170. The aspirated fluid passes through reservoir 175 and into drain bag 180.

During a phacoemulsification procedure, the tip of the needle can become occluded with a lens particle. This creates a condition that is called an occlusion. During an occlusion, less fluid is generally aspirated from the eye. The vacuum pressure in aspiration line 155 builds up as a result of the occlusion. Accordingly, during an occlusion, aspiration pressure sensor 160 reads the increased vacuum that builds up in aspiration line 155. When the occlusion breaks (that is when the lens particle that causes the occlusion is broken up by the ultrasonic needle), a surge occurs. The built up vacuum in aspiration line 155 creates a sudden demand for fluid from the eye resulting in a rapid lowering of IOP and shallowing of the operating space within the eye. This can lead to a dangerous situation in which various structures of the eye can be damaged.

The squeeze band device of the present invention is capable of responding to this surge effect by increasing the irrigation pressure in irrigation line 140. When an occlusion breaks and a surge occurs, band 110 is tightened in response to the decrease in irrigation pressure sensed by irrigation pressure sensor 130. In this manner, the pressure and resulting operating space in eye 145 can be maintained at a relatively constant value.

Likewise, when an occlusion occurs, irrigation pressure may increase as the fluid aspirated from the eye decreases. An increase in irrigation fluid pressure detected by irrigation pressure sensor 130 can be used to control motor 105 (and attached band 110) to regulate the pressure in eye 145—that is to keep the pressure in eye 145 within acceptable bounds.

Figure 2:
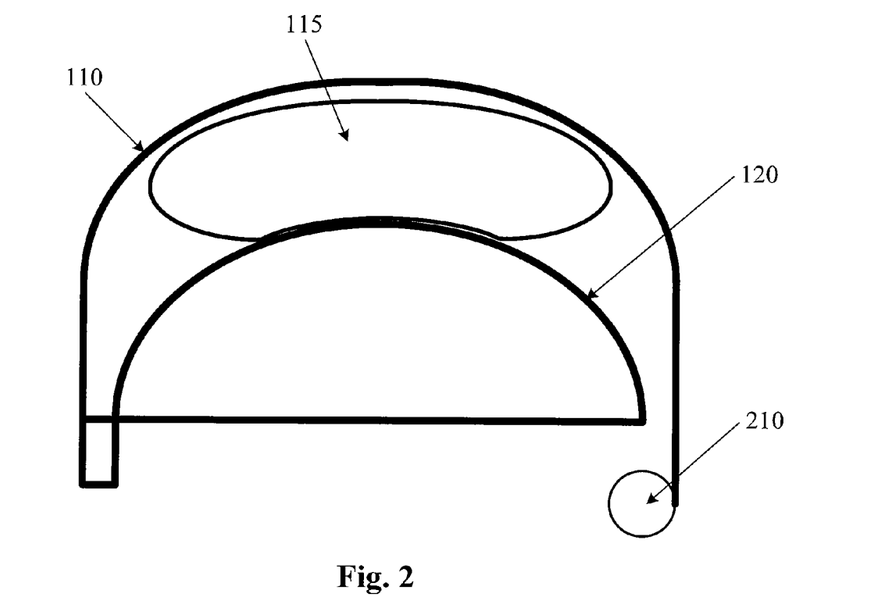
FIG. 2 is an end view of a pressurized irrigation squeeze band apparatus according to the principles of the present invention.

FIG. 2 is an end view of a pressurized irrigation squeeze band apparatus according to the principles of the present invention. In FIG. 2, bag 115 is held between band 110 and curved base 120. Shaft 210 is attached to motor 105 (not shown). Motor 105 turns shaft 210 to tighten (or loosen, as the case may be) band 110. When motor 105 is a DC motor or stepper motor, shaft 210 can be turned precisely to apply a known amount of force on bag 115. The force placed on bag 115 by band 110 is proportional to the pressure of the irrigation fluid in the irrigation line to which bag 115 is connected. The tension of band 110 forces the bag 115 to conform to the convex curve shape of the curved base 120. There is a linear relationship between pressure in bag 115 and the tension in band 110 approximated by the hoop stress formula:

$$\sigma_h = Pr/t$$

where $\sigma_h$=hoop stress (in this case, band stress from tension on the band 110)

P=internal pressure (in this case, pressure in the bag 115)

t=thickness of the hoop (in this case, the thickness of band 110)

r=the inside radius of the circle (in this case, the radius of curved base 120)

Band 110 can be made of a flexible but non-stretching material such as a thin flexible metal or plastic sheet, woven material, or other suitable material. In one embodiment, band 110 is made of a 0.010 inch thick UHMW polyethylene sheet.

Figure 3:
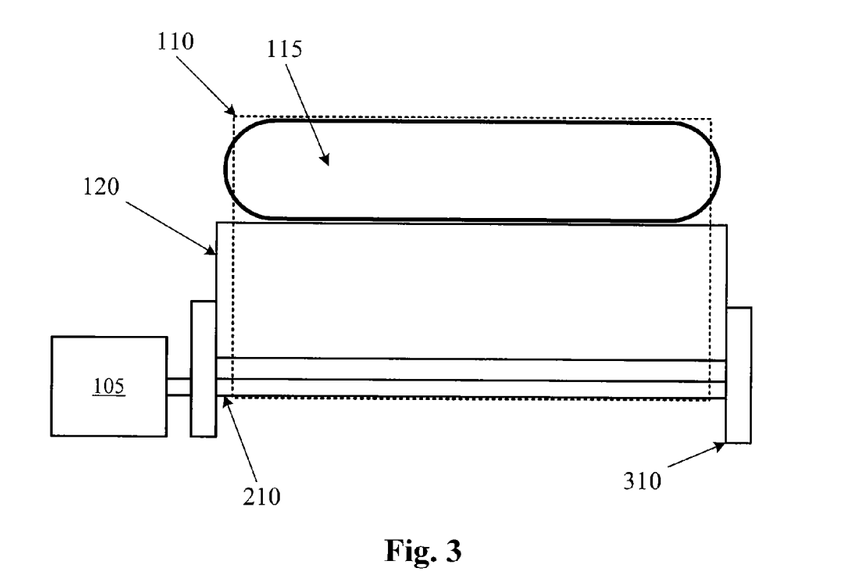
FIG. 3 is a side view of a pressurized irrigation squeeze band apparatus according to the principles of the present invention.

FIG. 3 is a side view of a pressurized irrigation squeeze band apparatus according to the principles of the present invention. In FIG. 3, bag 115 is held between band 110 and curved base 120. Curved base 120 is mounted to frame 125. Shaft 210 is coupled to motor 105. As motor 105 turns shaft 210, band 110 is tightened (or loosened depending on the direction that shaft 210 is turned). By controlling the operation of motor 105, the pressure in the eye 145 can be maintained within acceptable bounds.

Figure 4:
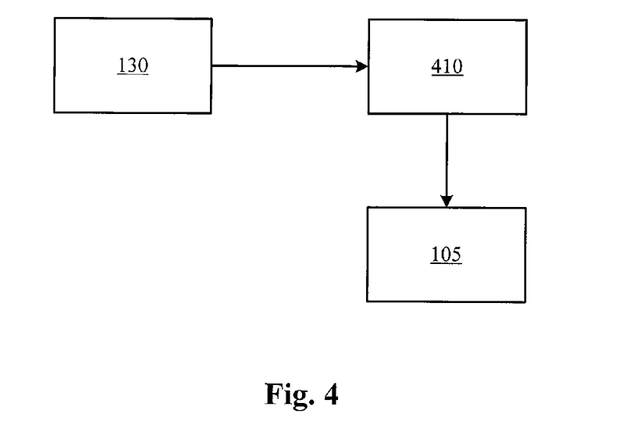
FIG. 4 is a block diagram of a pressurized irrigation squeeze band apparatus according to the principles of the present invention.

FIG. 4 is a block diagram of a pressurized irrigation squeeze band apparatus according to the principles of the present invention. In FIG. 4, a controller 410 receives an input from irrigation pressure sensor 130 and controls the operation of motor 105. In this manner, controller 410 controls motor 105 to adjust irrigation pressure. Controller 410 is typically an integrated circuit with power, input, and output pins capable of performing logic functions. In various embodiments, controller 410 is a targeted device controller. In such a case, controller 410 performs specific control functions targeted to a specific device or component, such as a motor. For example, motor controller has the basic functionality to control motor. In other embodiments, controller 410 is a microprocessor. In such a case, controller 410 is programmable so that it can function to control more than one component of the device. In other cases, controller 410 is not a programmable microprocessor, but instead is a special purpose controller configured to control different components that perform different functions. While depicted as one component in FIG. 4, controller 410 may be implemented by many different components or integrated circuits.

Figure 5:
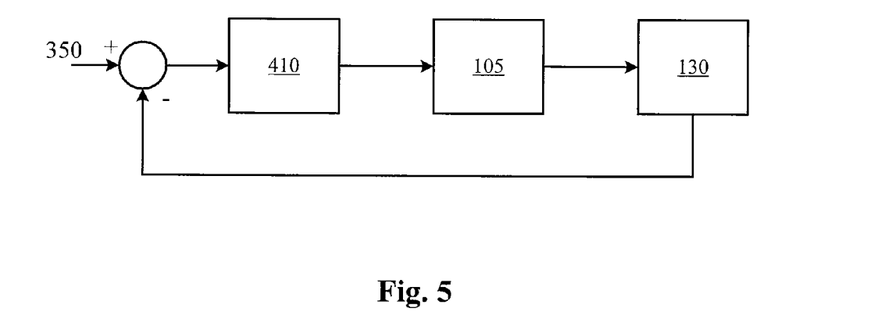
FIG. 5 is a block diagram of control system for a pressurized irrigation squeeze band apparatus according to the principles of the present invention.

FIG. 5 is a block diagram of control system for a pressurized irrigation squeeze band apparatus according to the principles of the present invention. In FIG. 5, an input 350 represents the desired pressure. In this example, controller 410 is a PID controller that controls the operation of motor 105. The irrigation pressure sensor 130 provides an input to controller 410. Controller 410 tracks the desired pressure (input 350) by controlling motor 105. For example, if the irrigation pressure is too low (lower than the desired pressure), controller 410 directs motor 105 to tighten band 110 thereby increasing the pressure in bag 115 (and the irrigation line to which bag 115 is coupled). If the irrigation pressure is too high (higher than the desired pressure), controller 410 directs motor 105 to loosen band 110 thereby decreasing the pressure in bag 115 (and the irrigation line to which bag 115 is coupled).

Figure 6:
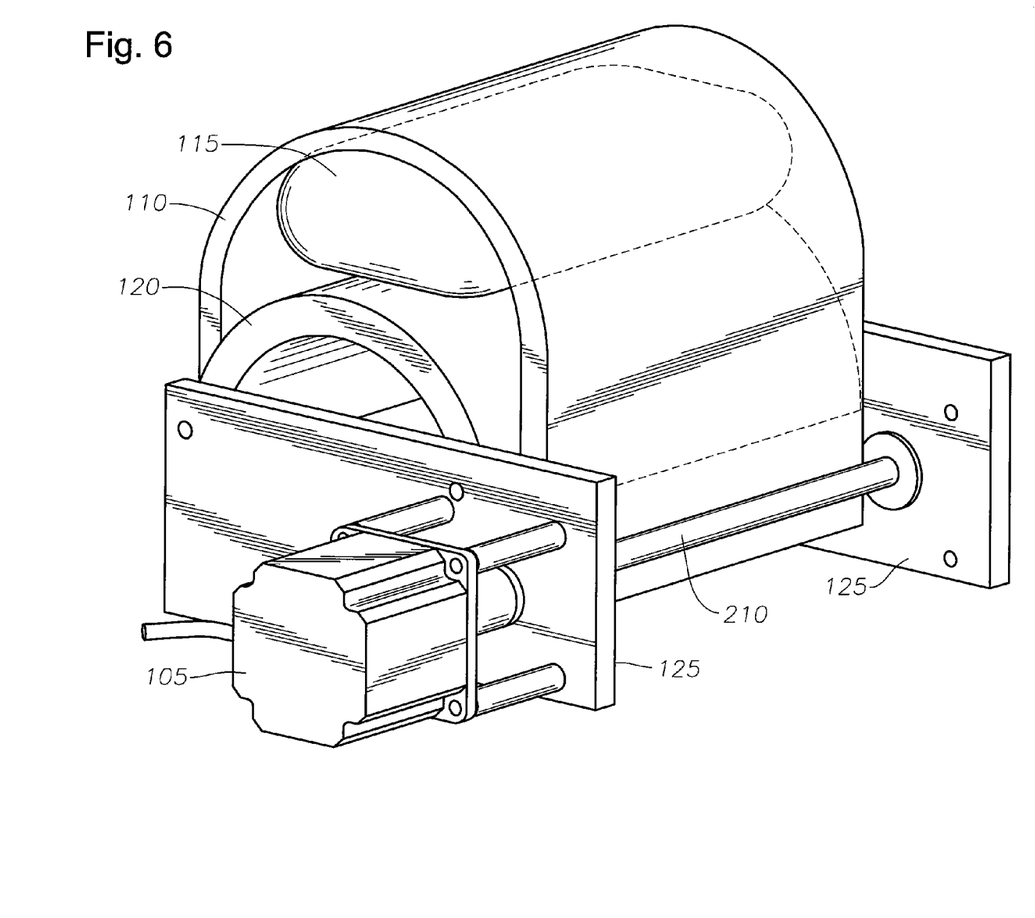
FIG. 6 is a perspective view of a pressurized irrigation squeeze band apparatus according to the principles of the present invention.

FIG. 6 is a perspective view of a pressurized irrigation squeeze band apparatus according to the principles of the present invention. In FIG. 6, bag 115 is held between band 110 and curved base 120. Curved base 120 is mounted to frame 125. Shaft 210 is coupled to motor 105.

Figure 7:
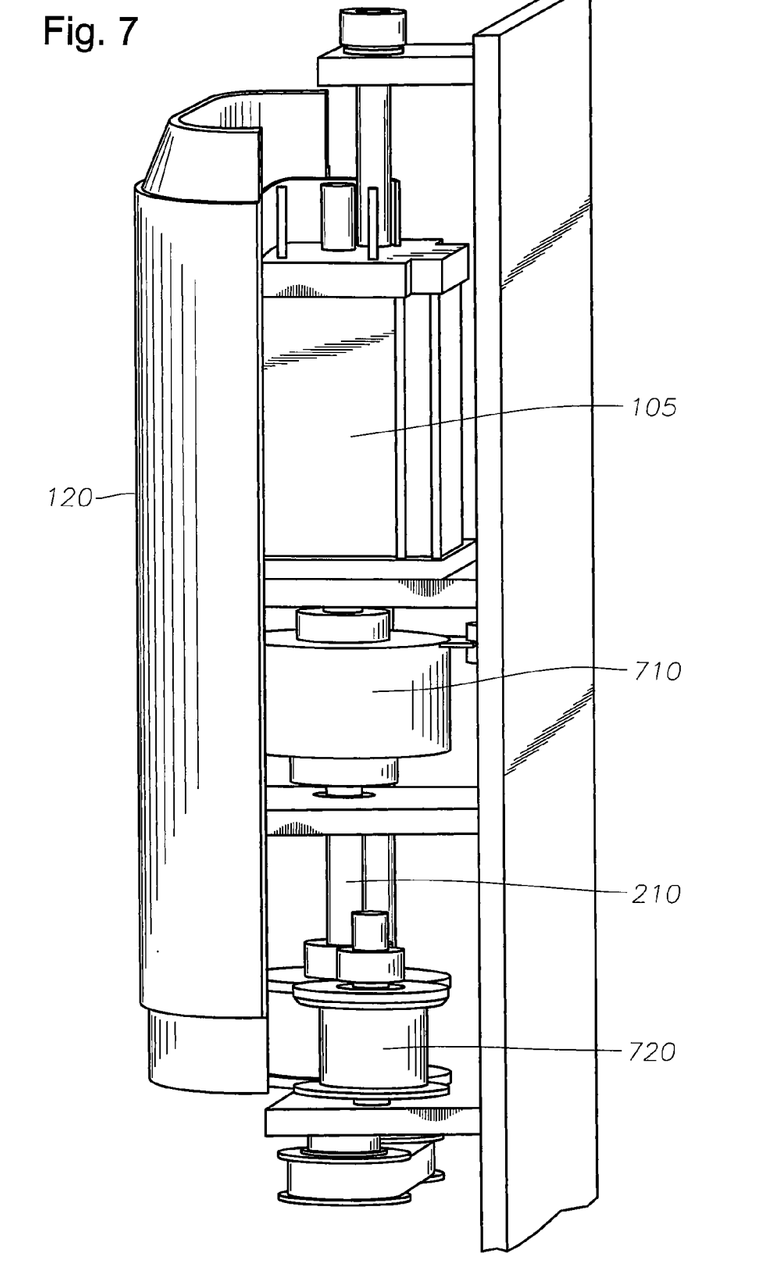
FIG. 7 is a side view of a pressurized irrigation squeeze band apparatus according to the principles of the present invention.

FIG. 7 is a side view of a pressurized irrigation squeeze band apparatus according to the principles of the present invention. In FIG. 7, motor 105 and curved base 120 are as described above. Clutch 710 is coupled to motor 105. Spring 720 is coupled to shaft 210. Clutch 710 engages or disengages the motor 105 and shaft 210. In this manner, clutch 710 provides a safety feature allowing for the shaft 210 to be disengaged from motor 105 if necessary. Spring 720 provides a constant torque on shaft 210 if motor 105 disengages from shaft 210. In this manner, if clutch 710 disengages motor 105 from shaft 210, then spring 720 provides a constant torque on shaft 210 to maintain a constant minimum pressure in the irrigation line (and the eye).

The irrigation squeeze band device of the present invention provides for precise control of irrigation pressure (and pressure in the eye) during cataract surgery. Prior attempts at a squeeze bag type device included using two opposing plates between which the bag is placed. The plates are moved together to increase pressure in the bag. It was discovered, however, that the bag was susceptible to movement while located in between the plates. This movement caused the control of the pressure to be slower than in the squeeze band device of the present invention. In the present invention, band 110 holds bag 115 securely against curved base 120. This allows for quicker and more precise control of pressure.

In addition, the surface contact area of the bag and rigid plates would vary significantly at different bag fill levels. As a result, at different bag fill levels, significantly different forces would be required to produce the same pressure, thus making consistent device control more challenging. The present invention provides significant benefit in minimizing contact surface area variation throughout bag volume depletion. The band conforms to the bag surface on one side, keeping the area nearly constant. While the base to bag contact area somewhat varies, the variations are not as significant as in case of the flat plates.

From the above, it may be appreciated that the present invention provides a pressurized infusion system for phacoemulsification surgery. The present invention provides an irrigation squeeze band device that more precisely controls fluid pressure. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pressurized infusion device for an ophthalmic surgical machine, the pressurized infusion device comprising:
   a flexible band having first and second ends;
   a curved base;
   a bag containing irrigating fluid, the bag located between the flexible band and the curved base;
   an irrigation line coupled to the bag;
   a pressure sensor for reading pressure in the irrigation line;
   a motor coupled to a shaft, the second end of the band coupled to the shaft;
   a spring coupled to the shaft, the spring providing a torque on the shaft; and
   a controller, the controller receiving an input from the irrigation pressure sensor to control the motor;

wherein when the motor is actuated to turn the shaft, tension is produced in the band to change pressure in the bag.

2. The device of claim 1 wherein the motor is controlled to maintain fluid pressure in an eye during cataract surgery within a range of fluid pressures.

3. The device of claim 1 wherein the flexible band is made of a thin, non-stretching material.

4. The device of claim 1 further comprising:
a clutch coupled to the motor to disengage the motor from the shaft.

5. The device of claim 1 wherein the first end of the flexible band is secured so that it is stationary relative to the curved base.

6. The device of claim 1 further comprising:
a frame coupled to the curved base.

7. The device of claim 1 wherein the pressure sensor also reads pressure in the bag.

8. The device of claim 1 further comprising:
a valve fluidly coupled to the irrigation line.

* * * * *